United States Patent [19]

Iino et al.

[11] Patent Number: 5,463,078
[45] Date of Patent: Oct. 31, 1995

[54] ANISOMYCIN DERIVATIVES AND ANTICANCER AGENTS, ANTIFUNGAL AGENTS AND ANTIPROTOZOAN AGENTS CONTAINING THE SAME

[75] Inventors: Yukio Iino; Makoto Ishii; Koji Ohsumi; Takashi Tsuji, all of Kawasaki, Japan

[73] Assignee: Ajinomoto Co., Inc., Tokyo, Japan

[21] Appl. No.: 196,508

[22] Filed: Feb. 15, 1994

[30] Foreign Application Priority Data

Feb. 15, 1993 [JP] Japan ..................... 5-025447
Nov. 24, 1993 [JP] Japan ..................... 5-293059

[51] Int. Cl.$^6$ .................. C07D 207/12; C12P 17/10; C12N 1/20; C12R 1/465
[52] U.S. Cl. ................................................. 548/541
[58] Field of Search ........................ 548/541; 514/425

[56] References Cited

FOREIGN PATENT DOCUMENTS 0464656 1/1992 European Pat. Off. .

OTHER PUBLICATIONS

The Journal of Organic Chemistry, vol. 51, No. 7, Apr. 4, 1986, Hideo Iida, et al., "Highly Selective Total Synthesis of Enantiomerically Pure (−)-Anisomycin", pp. 1069–1073.
Chemical Abstracts, vol. 107, No. 25, Dec. 21, 1987, AN 236368e, JP-A-6 289 659.
Helvetica Chimica Acta, vol. 53, No. 4, 1970, I. Felner, et al., "Totalsynthese Des Antibioticums Anisomycin", pp. 754–763.
The Journal of Organic Chemistry, vol. 57, No. 4, Feb. 14, 1992, Roberto Ballini, et al., "A Nitrone-Based Approach to the Enantioselective Total Synthesis of (−)-Anisomycin", pp. 1316–1318.
The Journal of Organic Chemistry, vol. 53, No. 20, Sep. 30, 1988, Hans H. Baer, et al., "Stereospecific Synthesis of (−)-Anisomycin from D-Galactose", pp. 4786–4789.

Primary Examiner—David B. Springer
Attorney, Agent, or Firm—Oblon, Spivak, McClelland, Maier, & Neustadt

[57] ABSTRACT

Anisomycin derivatives represented by the following formula:

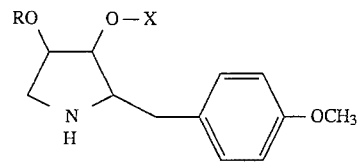

and salts thereof, wherein R is hydrogen or an acyl group of 1–18 carbon atoms, and X is either a carbamoyl group represented by the formula —CONR$^1$R$^2$ or an alkyl group represented by the formula —CH$_2$R$^3$ in which R$^1$ and R$^2$ are each hydrogen, a linear or cyclic alkyl group of 1–6 carbon atoms which may have a substituent or a phenyl group which may have a substituent, and R$^3$ is hydrogen, an alkyl group of 1–6 carbon atoms or an alkoxy group of 1–6 carbon atoms which may have a substituent, have improved stability in blood or plasma and are useful as anticancer agents, antifungal agents and antiprotozoan agents.

15 Claims, No Drawings

ANISOMYCIN DERIVATIVES AND ANTICANCER AGENTS, ANTIFUNGAL AGENTS AND ANTIPROTOZOAN AGENTS CONTAINING THE SAME

This application claims priority under 35 U.S.C. §119 to each of Japanese Patent Application Nos. 025447/1993 and 293059/1993, filed in Japan on Feb. 15, 1993 and Nov. 24, 1993, respectively, each of which is incorporated herein by reference.

BACKGROUND OF THE INVENTION

1. Field of the Invention

The present invention relates to novel anisomycin derivatives, to pharmaceutical compositions containing an effective amount of the same to treat cancer or to treat and/or prevent infections by fungi and/or protozoa, and to methods of treating cancer, treating and/or preventing infection by fungi and/or protozoa, and killing fungi and/or protozoa.

2. Discussion of the Background

Anisomycin is an antibiotic having the structure shown in formula (I) below. Anisomycin is produced by actinomycetes, and it is known to have strong cytotoxic activity due to its inhibitory effect on protein synthesis (*J. Biol. Chem.*, vol. 242, p. 3226, 1967).

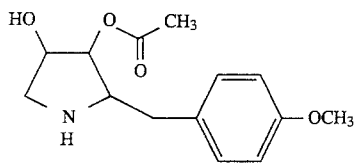

The application of anisomycin or derivatives thereof as anticancer agents, antifungal agents, antiprotozoan agents and the like has been attempted. For example, there is a description in Japanese Patent Application Laid-Open No. 62-89659 regarding the anticancer effect of a 3- or 4-acyloxy substituted anisomycin. However these derivatives have a low effect in vivo compared with their strong cytotoxic activity in vitro. Thus, they are not practical for use as medicines, and the need for anisomycin derivatives which exhibit strong in vivo anticancer, antifungal and antiprotozoan activities is still felt.

SUMMARY OF THE INVENTION

One object of the present invention is to provide novel anisomycin derivatives which have strong antitumor activity in vivo.

Another object of the present invention is to provide novel anisomycin derivatives which have strong antifungal activity in vivo.

Another object of the present invention is to provide novel anisomycin derivatives which have strong antiprotozoan activity in vivo.

Another object of the present invention is to provide a method of treating cancer, treating and/or preventing infection by fungi and/or protozoa, and killing fungi and/or protozoa using the present anisomycin derivatives.

These and other objects, which will become apparent from the following detailed description of the preferred embodiments, have been realized by the present invention, which provides an anisomycin derivative of the following formula or a salt thereof:

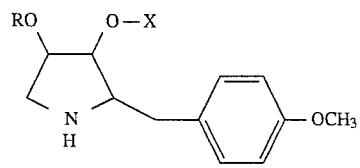

wherein R is a hydrogen atom or an acyl group having 1 to 18 carbon atoms; and X is either a carbamoyl group of the formula —$CONR^1R_2$ or an alkyl group of the formula —$CH_2R^3$, wherein each of $R^1$ and $R^2$ is independently a hydrogen atom, a linear or cyclic alkyl group having 1 to 6 carbon atoms which may be substituted, or a phenyl group which may be substituted, and $R^3$ is a hydrogen atom, an alkyl group having 1 to 6 carbon atoms, or an alkoxy group having 1 to 6 carbon atoms which may be substituted.

DETAILED DESCRIPTION OF THE PREFERRED EMBODIMENTS

The present Inventors have discovered that anisomycin (the compound of formula (I) above) is extremely unstable in the blood and is rapidly hydrolyzed, causing deacetylization, by which it loses its activity. This instability has not been overcome, even for the compounds described in the above-mentioned publication.

The present Inventors have conducted much diligent research in order to overcome this problem. As a result, the present Inventors have discovered that a compound represented by formula (II) below, in which (1) the 3-acetyl ester group of anisomycin is converted to a carbamic ester or an ether group, and (2) the 4-hydroxyl group is modified, is more stable in the blood than anisomycin, and exhibits strong activity.

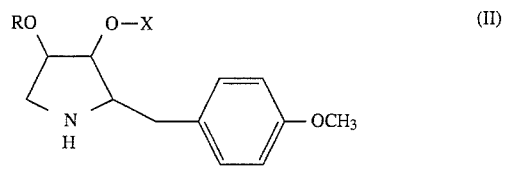

In formula (II), R is a hydrogen atom or an acyl group having 1 to 18 carbon atoms; and X is either a carbamoyl group of the formula —$CONR^1R^2$ or an alkyl group of the formula —$CH_2R^3$, wherein each of $R^1$ and $R^2$ is independently a hydrogen atom, an optionally substituted linear or cyclic alkyl group having 1 to 6 carbon atoms, or an optionally substituted phenyl group, and $R^3$ is a hydrogen atom, an alkyl group having 1 to 6 carbon atoms, or an optionally substituted alkoxy group having 1 to 6 carbon atoms.

In formula (II), the acyl group represented by R is a saturated or unsaturated alkylcarbonyl group having 1 to 18 carbon atoms (i.e., a group of the formula R'—C(=O)—, in which R' is H or an alkyl, alkenyl or alkynyl group of from 1 to 17 carbon atoms). The alkyl portion of the acyl group may be linear, branched, or cyclic, and may contain one or more unsaturated carbon-carbon bonds.

When $R^1$ and/or $R^2$ is/are a substituted alkyl group, suitable substituents include one or more halogen atoms, hydroxy groups, carboxy groups, alkoxy groups of 1 to 4 carbon atoms, cyano groups, etc. When $R^1$ and/or $R^2$ is/are a substituted phenyl group, suitable substituents include those mentioned above for the substituted alkyl group, and further include alkyl, alkenyl and alkynyl groups of from 1 to 6 carbon atoms, which may be further substituted with from 1 to 3 halogen atoms. When $R^3$ is a substituted alkoxy group having 1 to 6 carbon atoms, suitable substituents include those mentioned above for the substituted phenyl group. Preferably, the substituted alkyl, phenyl and alkoxy groups contain from 1 to 3 substituents.

In formula (II), X is a carbamoyl group which may be substituted, an alkyl group or an optionally substituted alkoxy-alkyl group. Examples of suitable carbamoyl groups include carbamoyl, methylcarbamoyl, ethylcarbamoyl, propylcarbamoyl, (3-phenylpropyl)carbamoyl, cyclopropylcarbamoyl, dimethylcarbamoyl, (2-hydroxyethyl)carbamoyl, (2-dimethylaminoethyl)carbamoyl, (3-dimethylaminopropyl)carbamoyl, phenylcarbamoyl, etc. Examples of suitable alkyl groups include, for example, methyl, ethyl, propyl, isopropyl, butyl, isobutyl, pentyl, hexyl, heptyl, etc. Examples of suitable alkoxyalkyl groups include, for example, methoxymethyl, ethoxymethyl, propoxymethyl, butoxymethyl, pentoxymethyl, hexyloxymethyl, 2-methoxyethoxymethyl, etc.

Representative examples of the present anisomycin derivatives are given below:

3-O-carbamoyldeacetylanisomycin, 3-O-methylcarbamoyldeacetylanisomycin, 3-O-ethylcarbamoyldeacetylanisomycin, 3-O-propylcarbamoyldeacetylanisomycin, 3-O-(3-phenylpropyl)carbamoyldeacetylanisomycin, 3-O-cyclopropylcarbamoyldeacetylanisomycin, 3-O-dimethylcarbamoyldeacetylanisomycin, 3-O-(2-hydroxyethyl)carbamoyldeacetylanisomycin, 3-O-(2-dimethylaminoethyl)carbamoyldeacetylanisomycin, 3-O-(3-dimethylaminopropyl)carbamoyldeacetylanisomycin, 3-O-phenylcarbamoyldeacetylanisomycin, 4-O-acetyl-3-O-methylcarbamoyldeacetylanisomycin, 4-O-heptanoyl-3-O-methylcarbamoyldeacetylanisomycin, 4-O-octadecanoyl-3-O-methylcarbamoyldeacetylanisomycin, 4-O-acetyl-3-O-carbamoyldeacetylanisomycin, 4-O-hexanoyl- 3-O-carbamoyldeacetylanisomycin, 4-O-heptanoyl-3-O-carbamoyldeacetylanisomycin, 4-O-dodecanoyl-3-O-carbamoyldeacetylanisomycin, 4-O-octadecanoyl-3-O-carbamoyldeaetylanisomycin, 3-O-methyldeacetylanisomycin, 3-O-ethyl-deacetylanisomycin, 3-O-methoxymethyldeacetylanisomycin, 3-O-(2-methoxyethoxy)methyldeacetylanisomycin, etc.

These compounds may be in the form of a salt, including pharmaceutically acceptable salts. Examples of such salts include salts with inorganic acids such as hydrochloric acid, sulfuric acid, nitric acid, phosphoric acid, etc., and salts with organic acids such as acetic acid, lactic acid, citric acid, tartaric acid, maleic acid, fumaric acid, monomethylsulfuric acid, etc.

Many methods are suitable for the production of the present compounds. Examples of preferred methods are given below.

The compound of formula (II) in which X is —$CONR^1R^2$ (where $R^1$ and $R^2$ are as defined previously) may be produced from anisomycin (1) according to the scheme shown below:

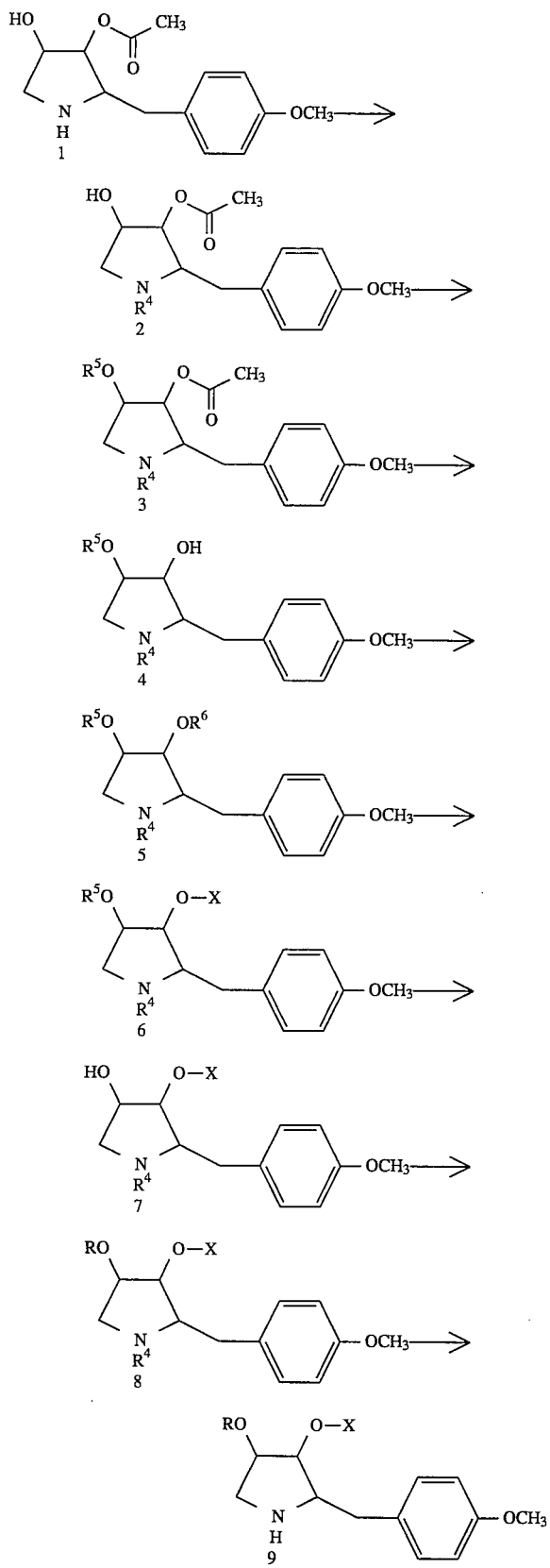

In this scheme, R and X are as defined previously, $R^4$ and $R^5$ are protecting groups, and $R^6$ is a carbonyl substituent.

More specifically, anisomycin (1) is protected at the 1-nitrogen with a conventional amino group-protecting group such as benzyloxycarbonyl, t-butoxycarbonyl, etc., and at the 4-hydroxy group with a conventional alcohol-protecting group such as a trimethylsilyl or t-butyldimethylsilyl group, etc., by conventional methodology. The 3-acetyl group is then hydrolyzed to obtain an intermediate compound (4). Thereafter, intermediate compound (4) is carboxylated with a carbonyl group-introducing reagent, such as phenyl chlorocarbonate, carbonyldiimidazole or the like, by conventional methodology, and an appropriate amine is further reacted therewith to obtain a compound (6). The 4-protecting group is then removed, and if desired or necessary, the 4-hydroxy group is acylated using an acylating agent such as an acid chloride, an acid anhydride, or the like, each by conventional methodology. Thereafter, the protecting group on the nitrogen is removed, thus providing the object compound (9).

Alternatively, the compound (6) may be produced directly by a reaction of the compound (4) and an isocyanate, in accordance with a conventional method.

The compound of formula (II) in which X is —CH$_2$R$^3$ (where R$^3$ is as defined previously) may be produced from the above-mentioned intermediate compound (4) according to the scheme shown below:

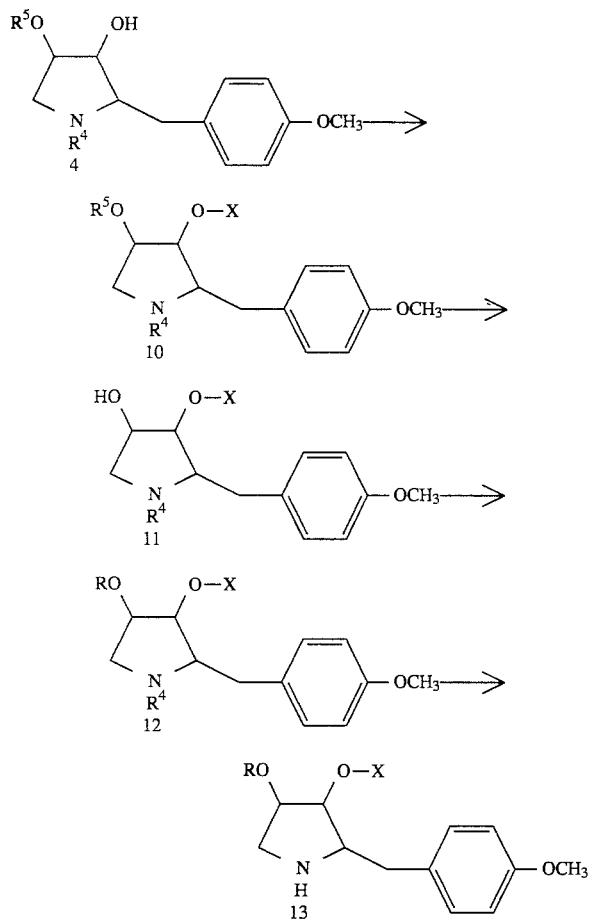

In this scheme, R$^4$, R$^5$, R and X are as defined previously.

More specifically, the 3-hydroxy group of the above mentioned intermediate compound (4) is alkylated using an alkyl halide, alkyl sulfate, etc. The 4-protecting group is then removed to produce compound (11). Then, if desired or if necessary, the 4-hydroxy group is acylated using an acylating agent such as an acid chloride, an acid anhydride, or the like. The protecting group on the nitrogen is then removed, thus providing object compound (13).

A compound according to the present invention which is obtained in this manner is stable in the blood, and exhibits strong anticancer, antifungal, and antiprotozoan activity. Thus, the present compounds are effective for use as an anticancer agent, antifungal agent or antiprotozoan agent.

Both in vivo and in vitro uses of the present compounds and of compositions containing the same are envisioned. Patients which can be treated in vivo with the present compounds include both humans and animals, such as domestic fowl and mammals (rabbits, dogs, cats, sheep, cows, pigs, etc.).

Examples of in vitro uses include: methods of preventing fungal and/or protozoan infection in cell cultures, comprising adding an effective amount of the compound of the present invention to prevent the growth of a fungus or a protozoa to a cell culture; methods of preventing the growth of a fungus or a protozoa on a surface or in a medium, comprising applying an effective amount of the compound of the present invention to the surface or adding an effective amount of the compound to the medium to prevent the growth of the fungus or protozoa; etc.

The present compound may be in the form of a pharmaceutical composition, in which case the compound may be in the form of a pharmaceutically acceptable salt. When the present compound is used as an anticancer agent, antifungal agent or antiprotozoan agent, it is administered intravenously, orally, intracutaneously, or as an eye drop (perocularly) to a patient in need thereof. The effective dosage varies, depending on the symptoms and age of the patient and on the method of administration. However, preferably, the dosage is from 1 to 3,000 mg/kg/day.

The present compound (in the form of a pharmaceutical composition) may be combined with an appropriate preparation carrier for administration as an anticancer agent, antifungal agent or antiprotozoan agent.

The preparation may be in the form of an injection, tablet, granules, fine granules, dispersion, capsule, cream, suppository or the like. The preparation carrier may be, for example, lactose, glucose, D-mannitol, starch, crystalline cellulose, calcium carbonate, kaolin, gelatin, hydroxypropyl cellulose, hydroxypropylmethyl cellulose, polyvinylpyrrolidone, ethanol, carboxymethyl cellulose, carboxymethyl cellulose calcium, magnesium stearate, talc, acetyl cellulose, sucrose, titanium oxide, benzoic acid, p-hydroxybenzoic ester, sodium dehydroacetate, gum Arabic, gum tragacanth, methyl cellulose, egg yolk, a surfactant (which may be a pharmaceutically acceptable surfactant), a simple syrup, citric acid, distilled water, ethanol, glycerin, propylene glycol, macrogol, monohydrogen sodium phosphate, dihydrogen sodium phosphate, sodium phosphate, sodium chloride, phenol, thimerosal, sodium hydrogen sulfite, etc., or any pharmaceutically acceptable mixture thereof. The carriers are used in combination with a compound according to the present invention, depending on its preparation form and the mode of delivery or administration.

The effective amount of the present compound to be contained in the anticancer, antifungal or antiprotozoan composition will vary widely depending on the form of the preparation, and it is not particularly restricted. However, it is normally from 0.01 to 100 wt %, and preferably 1 to 100 wt % of the weight of the total composition.

Other features of the invention will become apparent in the course of the following descriptions of exemplary embodiments, which are given for illustration of the invention, and are not intended to be limiting thereof.

EXAMPLES

A more detailed explanation of the present invention will now be provided with reference to the following Examples. However the present invention is not limited to these Examples.

Example 1

Production of
3-O-methylcarbamoyl-deacetylanisomycin (R=H, X=CONHCH$_3$)

STEP 1 Production of 4-O-t-butyldimethylsilyl-N-carbobenzyloxyanisomycin

A 3 g (11.3 mmol) portion of anisomycin was dissolved in 70 ml of tetrahydrofuran. An aqueous solution (12 ml) containing 1.32 g (12.4 mmol) of sodium carbonate was added to the resulting solution. A toluene solution containing 30–35% benzyl chloroformate (7.1 g, 12.5–14.5 mmol) was added dropwise thereto while stirring and cooling on ice. The mixture was then stirred at room temperature for 1 hour. The reaction mixture was concentrated under reduced pressure. The product was then extracted with dichloromethane, and the extract was dried over sodium sulfate and filtered. The filtered extract was concentrated under reduced pressure, then further purified by silica gel chromatography to obtain 4.51 g of N-carbobenzyloxyanisomycin.

The N-carbobenzyloxyanisomycin was dissolved in 50 ml of dimethylformamide, 6.156 g of imidazole and 5.1 g of t-butyldimethylsilyl chloride were added to the resulting solution, and the mixture was stirred at room temperature for 2 hours. To the reaction mixture was added 150 ml of water, and the product was extracted 3 times using 50 ml of a mixed solvent (1:5 ethyl acetate:hexane). After drying over sodium sulfate, the extract was filtered, concentrated under reduced pressure and purified by silica gel medium pressure liquid column chromatography to obtain 6.15 g of 4-O-t-butyldimethylsilyl-N-carbobenzyloxyanisomycin.

$^1$H NMR (CDCl$_3$): δ=0.08 (6H, s), 0.82 (9H, s), 2.08 (3H, s), 2.83–3.20 (2H, m), 3.36 (1H, dd, J=11.2, 4.1 Hz), 3.40–3.47 (1H, m), 3.79 (3H, s), 3.85–3.95 (1H, m), 4.38–4.45 (1H, m), 4.76–4.90 (1H, m), 5.19 (2H, broad s), 6.75–6.85 (2H, broad), 6.97 (1H, broad d), 7.08 (1H, broad d), 7.30–7.41 (5H, m) . MS(FD): m/z 513 (M$^+$)

STEP 2 Production of 4-O-t-butyldimethylsilyl-N-carbobenzyloxy-deacetylanisomycin To a solution of 6.15 g of 4-O-t-butyldimethylsilyl-N-carbobenzyloxy-anisomycin in a mixed solvent containing 50 ml of ethanol and 10 ml of water, a 2N aqueous solution of sodium hydroxide (6.78 ml) was added while cooling on ice. The mixture was stirred at room temperature for 1 hour. The reaction mixture was then concentrated under reduced pressure, and neutralized with an aqueous solution of ammonium chloride. The product was extracted with dichloromethane. The extract was dried over sodium sulfate, filtered, and concentrated under reduced pressure to obtain 5.17 g of 4-O-t-butyldimethylsilyl-N-carbobenzyloxy-deacetylanisomycin.

$^1$H NMR (CDCl$_3$): δ=0.08 (6H, s), 0.82 (9H, s), 2.83–3.10 (2H, m), 3.32–3.40 (1H, m), 3.45–3.55 (1H, m), 3.79 (3H, s), 3.90–4.00 (1H, m), 4.10–4.23 (2H, m), 5.18 (2H, broad s), 6.75–6.85 (2H, broad), 7.04–7.44 (7H, m) MS(FD): m/z 471 (M$^+$)

STEP 3 Production of 4-O-t-butyldimethylsilyl-N-carbobenzyloxy-3-O-phenyloxycarbonyl-deacetylanisomycin To a solution of 5.17 g (11 mmol) of 4-O-t-butyldimethylsilyl-N-carbobenzoxydeacetylanisomycin in 100 ml of benzene, 2 ml (25 mmol) of pyridine and 2.35 g (15 mmol) of phenyl chloroformate were added. The mixture was then stirred at room temperature for 2 hours. The reaction mixture was filtered and concentrated under reduced pressure to obtain a crude product, which was then dissolved in 100 ml of ethyl acetate and washed twice with aqueous hydrochloric acid (pH 2), after which the solution was dried over sodium sulfate, filtered, and concentrated under reduced pressure. The concentrate was purified by silica gel column chromatography to obtain 6.28 g (1.06 mmol) of 4-O-t-butyldimethylsilyl-N-carbobenzyloxy-3-O-phenyloxycarbonyldeacetylanisomycin.

$^1$H NMR (CDCl$_3$): δ=0.08 (6H, s), 0.82 (9H, s), 2.91 (1H, dd, J=13.6, 9.3 Hz), 3.00–3.40 (2H, m), 3.44 (1H, dd, J=11.2, 4.1 Hz), 3.52 (1H, dd, 3=11.2, 5.3 Hz), 3.79 (3H, s), 4.02–4.08 (1H, m), 4.40–4.52 (1H, m), 4.75–4.86 (1H, m), 5.20 (2H, broad s), 6.75–6.85 (2H, m), 7.04–7.44 (12H, m) MS(FD): m/z 591 (M$^+$)

STEP 4 Production of 4-O-t-butyldimethylsilyl-N-carbobenzyloxy-3-O-methylcarbamoyldeacetyl-anisomycin To a solution of 1.18 g of 4-O-t-butyldimethylsilyl-N-carbobenzyloxy-3-O-phenyloxycarbonyldeacetylanisomycin in 35 ml of dimethylformamide, 1.5 ml of a 40% aqueous solution of methylamine was added. The mixture was then stirred at 60° C. for 30 minutes. To the reaction mixture were added 200 ml of ethyl acetate and 20 ml of hexane for extraction. The extract was dried over sodium sulfate, filtered, and concentrated under reduced pressure, and the residue was purified by silica gel medium pressure liquid chromatography to obtain 1.05 g of 4-O-t-butyldimethyl-silyl-N-carbobenzyloxy-3-O-methylcarbamoyldeacetylanisomycin.

$^1$H NMR (CDCl$_3$): δ=−0.02 (6H, s), 0.80 (9H, s), 2.80 (3H, d, J=4.9 Hz), 2.80–2.92 (1H, broad), 3.37 (1H, dd, J=11.4, 4.2 Hz), 3.42 (1H, dd, J=11.4, 5.4 Hz), 3.77 (3H, s), 3.93 (1H, broad q, J=4.7 Hz), 4.32–4.41 (1H, broad), 4.62–4.80 (1H, broad), 4.70–4.80 (1H, broad), 5.10–5.20 (2H, broad), 6.72–6.80 (2H, broad), 6.90–6.99 (1H, broad), 7.04–7.11 (1H, broad), 7.30–7.40 (5H, m). MS(FD): m/z 528 (M$^+$)

STEP 5 Production of N-carbobenzyloxy-3-O-methylcarbamoyldeacetylanisomycin

The product of Step 4 above was dissolved in 30 ml of tetrahydrofuran, and 10 ml of a 1N tetrahydrofuran solution of tetrabutylammonium fluoride was added to the solution while cooling on ice. The mixture was stirred for 40 minutes. 1 ml of acetic acid was added to the mixture, which was then concentrated under reduced pressure. The crude product was purified by silica gel medium pressure liquid column chromatography to obtain 0.75 g of N-carbobenzyloxy-3-O-methylcarbamoyldeacetylanisomycin.

$^1$H NMR (CDCl$_3$): δ=2.81 (3H, d, J=4.8 Hz), 2.80–3.15 (2H, m), 3.36–3.45 (1H, broad), 3.48–3.58 (1H, m), 3.78 (3H, s), 3.96–4.08 (1H, broad), 4.43 (1H, q, J=6.0 Hz), 4.78–4.86 (2H, broad), 5.04–5.20 (2H, broad), 6.76 (2H, d, J=8.4 Hz), 6.90–7.10 (2H, broad), 7.30–7.40 (5H, m). MS(FAB): m/z 415 (MH$^+$)

STEP 6 3-O-methylcarbamoyldeacetylanisomycin

To a solution of the product of Step 5 above in 30 ml of ethanol was added 0.2 g of 10% palladium on carbon. The mixture was stirred under a hydrogen atmosphere at room temperature for 30 minutes. The reaction mixture was filtered and then concentrated under reduced pressure to obtain crystals, which were recrystallized from chloroform to obtain 0.47 g of 3-O-methylcarbamoyldeacetylanisomycin.

$^1$HNMR (DMSO-$d_6$): δ=2.50–2.59 (2H, m), 2.59 (3H, d, J=4.6 Hz), 2.65 (1H, dd, J=13.5, 6.8 Hz), 3.12 (1H, dd, J=11.7, 5.7 Hz), 3.31 (1H, td, J=7.2, 4.2 Hz), 3.71 (3H, s), 3.92–3.96 (1H, m), 4.54 (1H, dd, J=4.1, 1.2 Hz), 4.90–5.10 (1H, broad), 6.82 (2H, d, J=8.7 Hz), 7.01 (1H, q, J=4.5 Hz), 7.09 (2H, d, J=8.7 Hz). MS(FAB): m/z 281 (MH$^+$) High resolution mass spectrum (FAB): Measured: m/z 281.1512; Calculated: ($C_{14}H_{21}N_2O_4$) :MH 281.1502.

Examples 2–10 describe compounds produced according to the same method as described in Example 1.

Example 2

3-O-carbamoyldeacetylanisomycin (R=H, X=CONH$_2$)

$^1$H NMR (CDCl$_3$): δ=2.72 (1H, dd, J=13.7, 8.3 Hz), 2.73 (1H, dd, J=11.1, 4.7 Hz), 2.84 (1H, dd, J=13.7, 6.0 Hz), 3.42 (1H, dd, J=11.1, 6.4 Hz), 3.49 (1H, ddd, J=8.3, 6.0, 4.8 Hz), 3.78 (3H, s), 4.26 (1H, ddd, J=6.4, 4.7, 1.5 Hz), 4.66 (1H, dd, J=4.8, 1.5 Hz), 4.82–4.85 (2H, broad), 6.83 (2H, d, J=8.6 Hz), 7.11 (2H, d, J=8.6 Hz) MS(FAB): m/z 267 (MH$^+$) High resolution mass spectrum (FAB): Measured: m/z 267.1348; Calculated ($C_{13}H_{19}N_2O_4$): MH 267.1345.

Example 3

3-O-ethylcarbamoyldeacetylanisomycin (R=H, X=CONHCH$_2$CH$_3$)

$^1$H NMR ($d_6$-DMSO): δ=1.04 (3H, t, J=7.3 Hz), 2.53–2.62 (2H, m), 2.68 (1H, dd, J=13.2, 7.0 Hz), 3.02 (1H, quint, J=6.6 Hz), 3.14 (1H, dd, J=11.9, 5.9 Hz), 3.34–3.40 (1H, m), 3.71 (3H, s), 3.94–3.97 (1H, broad), 4.55 (1H, d, J=3.5 Hz), 5.02–5.14 (1H, broad), 6.82 (2H, d, J=8.6 Hz), 7.11 (2H, d, J=8.6 Hz), 7.15 (1H, t, J=6.0 Hz). MS(FAB): m/z 295 (MH$^+$) High resolution mass spectrum(FAB): Measured: m/z 295.1677; Calculated ($C_{15}H_{23}N_2O_4$): MH 295.1658.

Example 4

3-O-propylcarbamoyldeacetylanisomycin (R=H, X=CONHCH$_2$CH$_2$CH$_3$)

$^1$H NMR (CDCl$_3$): δ=0.96 (3H, t, J=7.2 Hz), 1.50–1.62 (2H, m), 2.74 (1H, dd, J=14.0, 8.8 Hz), 2.75 (1H, dd, J=11.6, 4.9 Hz), 2.86 (1H, dd, J=14.0, 5.9 Hz), 3.18 (1H, q, J=7.2 Hz), 3.42 (1H, dd, J=11.6, 6.4 Hz), 3.48–3.56 (1H, m), 3.79 (3H, s), 4.25 (1H, ddd, J=6.4, 4.9, 1.4 Hz), 4.69 (1H, dd, J=4.8, 1.4 Hz), 4.96 (1H, broad t, J=6.0 Hz), 6.84 (2H, d, J=8.5 Hz), 7.13 (2H, d, J=8.5 Hz) MS(FAB ): m/z 309 (MH$^+$) High resolution mass spectrum(FAB): Measured: m/z 309.1813; Calculated ($C_{16}H_{25}N_2O_4$): MH 309.1814

Example 5

3-O-(3-phenylpropyl)carbamoyldeacetylanisomycin (R=H, X=CONHCH$_2$CH$_2$CH$_2$C$_6$H$_5$)

$^1$H NMR (CDCl$_3$): δ=1.86 (2H, quint, J=7.5 Hz), 2.64–2.70 (3H, m), 2.72 (1H, dd, J=10.8, 5.1 Hz), 2.82 (1H, dd, J=13.3, 5.6 Hz), 3.23 (1H, q, J=6.6 Hz), 3.40 (1H, dd, J=10.8, 6.7 Hz), 3.48 (1H, dt, J=8.0, 5.2 Hz), 3.75 (3H, s), 4.00–4.08 (1H, broad ), 4.23 (1H, ddd, J=6.7, 5.1, 1.4 Hz), 4.66 (1H, dd, J=4.8, 1.4 Hz), 4.87 (1H, broad t, J=5.7 Hz), 6.83 (2H, d, J=8.1 Hz), 7.11 (2H, d, J=8.1 Hz), 7.16–7.22 (3H, m), 7.26–7.32 (2H, m) MS(FAB): m/z 385 (MH$^+$) High resolution mass spectrum(FAB): Measured: m/z 385.2123; Calculated ($C_{22}H_{29}N_2O_4$): MH 385.2127.

Example 6

3-O-cyclopropylcarbamoyldeacetylanisomycin (R=H, X=CONHC$_3$H$_5$)

$^1$H NMR (CDCl$_3$): δ=0.52–0.57 (2H, m), 0.72–0.79 (2H, m), 2.57–2.65 (1H, m), 2.71 (1H, dd, J=10.5, 5.0 Hz), 2.76–2.88 (1H, broad), 2.95–3.10 (1H, broad), 3.39 (1H, dd, J=11.3, 6.8 Hz), 3.42–3.52 (1H, m), 3.77 (3H, s), 4.23 (1H, td, J=5.7, 1.5 Hz), 4.67 (1H, dd, J=5.2, 1.5 Hz), 5.00–5.09 (1H, broad), 6.83 (2H, d, J=8.4 Hz), 7.11 (2H, d, J=8.4 Hz) MS(FAB): m/z 307 (MH$^+$) High resolution mass spectrum(FAB): Measured: m/z 307.1660; Calculated ($C_{16}H_{23}N_2O_4$): MH 307.1658

Example 7

3-O-dimethylcarbamoyldeacetylanisomycin (R=H, X=CON (CH$_3$)$_2$)

$^1$H NMR ($d_6$-DMSO): δ=2.47–2.53 (1H, m), 2.58 (1H, dd, J=13.5, 7.5 Hz), 2.64 (1H, dd, J=13.5, 6.9 Hz), 2.84 (3H, bs), 2.91 (3H, bs), 3.16 (1H, dd, J=11.7, 5.8 Hz), 3.24–3.30 (1H, m), 3.71 (3H, s), 3.90–3.95 (1H, m), 4.53 (1H, dd, J=3.7, 1.3 Hz), 4.97–5.01 (1H, broad), 6.82 (2H, d, J=8.5 Hz), 7.09 (2H, d, J=8.5 Hz) MS(FAB): m/z 295 (MH$^+$) High resolution mass spectrum(FAB): Measured: m/z 295.1661; Calculated ($C_{15}H_{23}N_2O_4$): MH 295.1658

Example 8

3-O-(2hydroxyethyl)carbamoyldeacetylanisomycin (R=H, X=CONHCH$_2$CH$_2$OH)

$^1$H NMR (CDCl$_3$): δ=2.66–2.78 (2H, m), 2.85 (1H, dd, J=13.8, 5.9 Hz), 3.32–3.38 (2H, m), 3.40 (1H, dd, J=11.2, 6.4 Hz), 3.48–3.58 (1H, m), 3.73 (2H, t, J=5.0 Hz), 3.78 (3H, s), 4.25 (1H, ddd, J=6.4, 4.7, 1.4 Hz), 4.71 (1H, dd, J=4.8, 1.4 Hz), 5.51 (1H, broad t, J=5.3 Hz), 6.83 (2H, d, J=8.3 Hz), 7.11 (2H, d, J=8.3 Hz) MS(FAB): m/z 311 (MH$^+$) High resolution mass spectrum(FAB): Measured: m/z 311.1603; Calculated ($C_{15}H_{23}N_2O_5$): MH 311.1607

Example 9

3-O-(2-dimethylaminoethyl)carbamoyldeacetylanisomycin (R=H, X=CONHCH$_2$CH$_2$N(CH$_3$)$_2$)

$^1$H NMR (CDCl$_3$): δ=2.26 (6H, s), 2.45 (2H, t, J=5.9 Hz), 2.74 (1H, dd, J=13.8, 8.3 Hz), 2.79 (1H, dd, J=11.4, 4.6 Hz), 2.87 (1H, dd, J=13.8, 6.0 Hz), 3.29 (2H, q, J=5.6 Hz), 3.42 (1H, dd, J=11.4, 6.2 Hz), 3.55–3.60 (1H, m), 3.77 (3H, s), 4.25 (1H, ddd, J=6.2, 4.6, 1.2 Hz), 4.70 (1H, dd, J=4.6, 1.2 Hz), 5.62 (1H, broad t, J=4.7 Hz), 6.82 (2H, d, J=8.5 Hz), 7.12 (2H, d, J=8.5 Hz) MS(FAB): m/z 338 (MH$^+$) High resolution mass spectrum(FAB): Measured: m/z 338.2083; Calculated ($C_{17}H_{28}N_3O_4$): MH 338.2080

Example 10

3-O-(3-dimethylaminopropyl)carbamoyldeacetylanisomycin (R=H, X=CONHCH$_2$CH$_2$CH$_2$N(CH$_3$)$_2$)

$^1$H NMR (CDCl$_3$): δ=1.67 (2H, t, J=6.4 Hz), 2.22 (6H, s), 2.36 (2H, t, J=6.6 Hz), 2.65–2.76 (2H, m), 2.84 (1H, dd, J=14.0, 5.9 Hz), 3.28 (2H, q, J=6.1 Hz), 3.40 (1H, dd, J=11.2, 6.7 Hz), 3.45–3.54 (1H, m), 3.79 (3H, s), 4.23 (1H, ddd, J=6.7, 5.4, 1.7 Hz), 4.66 (1H, dd, J=4.7, 1.7 Hz), 5.84 (1H, broad t, J=5.1 Hz), 6.82 (2H, d, J=8.5 Hz), 7.12 (2H, d, J=8.5 Hz) MS(FAB): m/z 352 (MH$^+$) High resolution mass spectrum(FAB): Measured: m/z 352.2232; Calculated (C$_{18}$H$_{30}$N$_3$O$_4$): MH 352.2236

Example 11

Production of 3-O-phenylcarbamoyldeacetylanisomycin (R=H, X=CONHC$_6$H$_5$)

To a solution of 0.05 g of 4-O-t-butyldimethylsilyl-N-carbobenzyloxydeacetylanisomycin in 2 ml of benzene, 0.14 g of pyridine and 0.081 g of phenyl isocyanate were added. The resulting solution was then stirred at room temperature for 24 hours. The reaction mixture was concentrated under reduced pressure, dichloromethane was added thereto, and the insolubles were filtered off. The resulting solution was purified using silica gel thin layer chromatography to obtain 46 mg of 4-O-t-butyldimethylsilyl-N-carbobenzyloxy-3-O-phenylcarbamoyldeacetylanisomycin. The same procedures as in Steps 5 and 6 of Example 1 were carried out to obtain 9 mg of 3-O-phenylcarbamoyldeacetylanisomycin.

$^1$H NMR (CDCl$_3$, 400 MHz): δ=2.77 (1H, dd, J=11.3, 4.7 Hz), 2.78 (1H, dd, J=13.3, 8.0 Hz), 2.90 (1H, dd, J=13.3, 5.6 Hz), 3.46 (1H, dd, J=11.3, 6.6 Hz), 3.55 (1H, ddd, J=8.0, 5.6, 4.7 Hz), 3.79 (3H, s), 4.33 (1H, dd, J=6.6, 4.7 Hz), 4.80 (1H, d, J=4.7 Hz), 6.83 (2H, d, J=8.6 Hz), 7.10 (1H, t, J=7.7 Hz), 7.14 (2H, d, J=8.6 Hz), 7.34 (2H, t, J=7.7 Hz), 7.40 (2H, d, J=7.7 Hz) MS(FAB): m/z 343 (MH$^+$) High resolution mass spectrum(FAB): Measured: m/z 343.1671; Calculated (C$_{19}$H$_{23}$N$_2$O$_4$): MH 343.1658

Example 12

Production of 4-O-acetyl-3-O-methylcarbamoylanisomycin (R=CH$_3$CO, X=CONHCH$_3$)

A 0.2 g (0.48 mmol) portion of the N-carbobenzyloxy-3-O-methylcarbamoyldeacetylanisomycin obtained in Step 4 of Example 1 was dissolved in 10 ml of benzene. 0.12 g (0.96 mmol) of dimethylaminopyridine and 0.1 g (0.96 mmol) of either acetic anhydride or acetyl chloride were added to the solution, and the mixture was then stirred at room temperature for 1 hour. The reaction mixture was then concentrated under reduced pressure, and the residue was purified using silica gel column chromatography to obtain N-carbobenzoxy-3-O-methylcarbamoylanisomycin. The same procedures as in Steps 5 and 6 of Example 1 were carried out to obtain 0.15 g of 3-O-methylcarbamoylanisomycin.

$^1$H NMR (CDCl$_3$): δ=2.04 (3H, s), 2.66 (1H, dd, J=13.4, 8.2 Hz), 2.73 (1H, dd, J=12.6, 3.8 Hz), 2.84 (3H, d, J=4.8 Hz), 2.86 (1H, dd, J=13.4, 5.4 Hz), 3.36–3.44 (1H, m), 3.56 (1H, dd, J=11.9, 6.2 Hz), 3.77 (3H, s), 4.73–4.81 (1H, broad), 5.06–5.11 (2H, m), 6.82 (2H, d, J=8.6 Hz), 7.13 (2H, d, J=8.6 Hz) MS(FAB): m/z 323 (MH$^+$) High resolution mass spectrum(FAB): Measured: m/z 323.1606; Calculated (C$_{16}$H$_{23}$N$_2$O$_5$): MH 323.1607

Examples 13–19 describe compounds produced according to the same method as described in Example 12.

Example 13

4-O-heptanoyl-3-O-methylcarbamoyldeacetylanisomycin (R=C$_6$H$_{13}$CO, X=CONHCH$_3$)

$^1$H NMR (CDCl$_3$): δ=0.87 (3H, t, J=6.9 Hz), 1.24–1.32 (6H, m), 1.59 (2H, quint, J=7.4 Hz), 2.27 (2H, t, J=7.4 Hz), 2.65 (1H, dd, J=13.7, 8.7 Hz), 2.70–2.80 (1H, broad), 2.83 (3H, d, J=4.7 Hz), 2.85 (1H, dd, J=13.7, 5.3 Hz), 3.34–3.43 (1H, broad), 3.55 (1H, dd, J=12.5, 6.4 Hz), 3.70 (3H, s), 4.72–4.81 (1H, broad), 5.05–5.10 (2H, m), 6.83 (2H, d, J=8.6 Hz), 7.12 (2H, d, J=8.6 Hz) MS(FAB): m/z 393 (MH$^+$) High resolution mass spectrum(FAB): Measured: m/z 393.2374; Calculated (C$_{21}$H$_{33}$N$_2$O$_5$): MH 393.2390

Example 14

4-O-octadecanoyl-3-O-methylcarbamoyldeacetylanisomycin (R=CH$_{17}$H$_{35}$CO, X=CONHCH$_3$)

$^1$H NMR (CDCl$_3$): δ=0.85 (3H, t, J=6.6 Hz), 1.18–1.30 (28H, m), 1.43–1.53 (2H, m), 2.26 (2H, t, J=7.2 Hz), 2.50–2.60 (2H, m), 2.59 (3H, d, J=4.6 Hz), 2.68 (1H, dd, J=13.3, 6.2 Hz), 3.20–3.37 (2H, m), 3.71 (3H, s), 4.71 (1H, broad d, J=4.2 Hz), 4.86–4.91 (1H, m), 6.82 (2H, d, J=8.5 Hz), 7.11 (2H, d, J=8.5 Hz) MS(FAB): m/z 547 (MH$^+$) High resolution mass spectrum(FAB): Measured: m/z 547.4093; Calculated (C$_{32}$H$_{55}$N$_2$O$_5$): MH 547.4111

Example 15

4-O-acetyl-3-O-carbamoylanisomycin (R=CH$_3$CO, X=CONH$_2$)

$^1$H NMR (CDCl$_3$): δ=2.04 (3H, s), 2.69 (1H, dd, J=13.8, 8.6 Hz), 2.74 (1H, dd, J=12.5, 3.6 Hz), 2.86 (1H, dd, J=13.8, 5.6 Hz), 3.40 (1H, ddd, J=8.6, 5.6, 4.1 Hz), 3.56 (1H, dd, J=12.5, 6.6 Hz), 3.78 (3H, s), 4.75–4.82 (2H, broad), 5.04 (1H, dd, J=4.1, 1.2 Hz), 5.09 (1H, ddd, J=6.6, 3.6, 1.2 Hz), 6.84 (2H, d, J=8.5 Hz), 7.13 (2H, d, J=8.5 Hz) MS(FAB): m/z 309 (MH$^+$) High resolution mass spectrum(FAB): Measured: m/z 309.1457; Calculated (C$_{15}$H$_{21}$N$_2$O$_5$): MH 309.1451

Example 16

4-O-hexanoyl-3-O-carbamoyldeacetylanisomycin (R=C$_5$H$_{11}$CO, X=CONH$_2$)

$^1$H NMR (CDCl$_3$): δ=0.88 (3H, t, J=7.0 Hz), 1.24–1.34 (4H, m), 1.59 (2H, quint, J=7.3 Hz), 2.27 (2H, t, J=7.6 Hz), 2.75 (1H, dd, J=13.7, 8.2 Hz), 2.77 (1H, dd, J=12.8, 3.4 Hz), 2.87 (1H, dd, J=13.7, 6.0 Hz), 3.44 (1H, ddd, J=8.2, 6.0, 4.0 Hz), 3.58 (1H, dd, J=12.8, 6.2 Hz), 3.77 (3H, s), 5.01 (1H, dd, J=4.0, 1.0 Hz), 5.06–5.12 (2H, broad), 5.11 (1H, ddd, J=6.2, 3.4, 1.0 Hz), 6.83 (2H, d, J=8.7 Hz), 7.13 (2H, d, J=8.7 Hz) MS(FAB): m/z 365 (MH$^+$) High resolution mass spectrum(FAB): Measured: m/z 365.2089; Calculated (C$_{19}$H$_{29}$N$_2$O$_5$): MH 365.2076

Example 17

4-O-heptanoyl-3-O-carbamoyldeacetylanisomycin
(R=C$_6$H$_{13}$CO, X=CONH$_2$)

$^1$H NMR (CDCl$_3$): δ=0.87 (3H, t, J=6.8 Hz), 1.24–1.32 (6H, m), 1.58 (2H, quint, J=7.2 Hz), 2.28 (2H, t, J=7.5 Hz), 2.68 (1H, dd, J=13.7, 8.7 Hz), 2.72 (1H, dd, J=12.4, 3.6 Hz), 2.86 (1H, dd, J=13.7, 5.6 Hz), 3.40 (1H, ddd, J=8.4, 5.5, 4.1 Hz), 3.56 (1H, dd, J=12.4, 6.4 Hz), 3.77 (3H, s), 4.75–4.82 (2H, broad), 5.04 (1H, dd, J=4.2, 1.2 Hz), 5.10 (1H, ddd, J=6.4, 3.6, 1.2 Hz), 6.84 (2H, d, J=8.6 Hz), 7.13 (2H, d, J=8.6 Hz) MS(FAB): m/z 379 (MH$^+$) High resolution mass spectrum(FAB): Measured: m/z 379.2235; Calculated (C$_{20}$H$_{31}$N$_2$O$_5$): MH 379.2233

Example 18

4-O-dodecanoyl-3-O-carbamoyldeacetylanisomycin
(R=C$_{11}$H$_{23}$CO, X=CONH$_2$)

$^1$H NMR (CDCl$_3$): δ=0.88 (3H, t, J=6.7 Hz), 1.20–1.35 (16H, broad s), 1.59 (2H, quint, J=7.1 Hz), 2.28 (2H, t, J=7.5 Hz), 2.79 (1H, dd, J=13.5, 8.2 Hz), 2.83 (1H, dd, J=12.5, 3.1 Hz), 2.93 (1H, dd, J=13.5, 6.0 Hz), 3.49 (1H, ddd, J=8.2, 6.0, 4.0 Hz), 3.62 (1H, dd, J=12.5, 6.3 Hz), 3.78 (3H, s), 4.78–4.88 (2H, broad), 5.04 (1H, dd, J=4.0, 1.0 Hz), 5.12 (1H, ddd, J=6.2, 3.1, 1.0 Hz), 6.85 (2H, d, J=8.6 Hz), 7.15 (2H, d, J=8.6 Hz) MS(FAB): m/z 449 (MH$^+$) High resolution mass spectrum(FAB): Measured: m/z 449.3013; Calculated (C$_{25}$H$_{41}$N$_2$O$_5$): MH 449.3017

Example 19

4-O-octadecanoyl-3-O-carbamoyldeacetylanisomycin
(R=C$_{17}$H$_{35}$CO, X=CONH$_2$)

$^1$H NMR (d$_6$-DMSO): δ=0.85 (3H, t, J=6.7 Hz), 1.16–1.30 (28H, broad), 1.42–1.54 (2H, m), 2.26 (2H, t, J=7.4 Hz), 2.55 (1H, dd, J=12.4, 3.1 Hz), 2.58 (1H, dd, J=13.6, 7.7 Hz), 2.70 (1H, dd, J=13.6, 6.6 Hz), 3.20–3.29 (1H, m), 3.34 (1H, dd, J=12.4, 6.3 Hz), 3.71 (3H, s), 4.68 (1H, dd, J=4.3, 1.5 Hz), 4.88 (1H, ddd, J=6.3, 3.1, 1.5 Hz), 6.57–6.67 (2H, broad), 6.82 (2H, d, J=8.7 Hz), 7.12 (2H, d, J=8.7 Hz) MS(FAB): m/z 533 (MH$^+$) High resolution mass spectrum(FAB): Measured: m/z 533.3954; Calculated (C$_{31}$H$_{53}$N$_2$O$_5$): MH 533.3954

Example 20

Production of 3-O-methyldeacetylanisomycin
(R=H, X=CH$_3$)

A 0.07 g (0.15 mmol) portion of the 4-O-t-butyldimethylsilyl-N-carbobenzyloxydeacetylanisomycin obtained in Example 1 was dissolved in 3.5 ml of dimethylformamide. 9 mg (0.02 mmol) of 60% sodium hydride and 0.02 ml (0.3 mmol) of methyl iodide were added to the solution and the mixture was stirred at room temperature for 1 hour. The reaction mixture was concentrated under reduced pressure and the residue was purified using silica gel thin layer chromatography to obtain 4-O-t-butyldimethylsilyl-N-carbobenzyloxy-3-O-methyldeacetylanisomycin. The same procedures as in Steps 5 and 6 of Example 1 were carried out to obtain 6 mg of 3-O-methyldeacetylanisomycin.

$^1$H NMR (CDCl$_3$): δ=2.69 (1H, d, J=12.2, 2.9 Hz), 2.73–2.79 (1H, m), 2.80 (1H, dd, J=12.2, 7.5 Hz), 2.86 (1H, dd, J=13.4, 7.7 Hz), 3.28–3.36 (1H, m), 3.38 (3H, s), 3.47 (1H, dd, J=12.5, 6.2 Hz), 3.80 (3H, s), 4.28 (1H, m), 6.83 (2H, d, J=8.7 Hz), 7.16 (2H, d, J=8.7 Hz) MS(FAB): m/z 238 (MH$^+$) High resolution mass spectrum(FAB): Measured: m/z 238.1443; Calculated (C$_{13}$H$_{20}$H)$_3$): MH 238.1449

Examples 21–23 describe compounds produced according to the same method as described in Example 20.

Example 21

3-O-ethyldeacetylanisomycin (R=H, X=CH$_2$CH$_3$)

$^1$H NMR (CDCl$_3$): δ=1.20–1.28 (3H, m), 2.80–2.95 (2H, m), 3.37–3.60 (3H, m), 3.50 (3H, s), 3.58–3.70 (2H, m), 3.78 (3H, s), 4.02 (1H, m), 4.28 (1H, m), 6.83 (2H, d, J=9.0 Hz), 7.15 (2H, d, J=9.0 Hz) MS(FAB): m/z 252 (MH$^+$) High resolution mass spectrum(FAB): Measured: m/z 252.1600; Calculated (C$_{14}$H$_{22}$NO$_3$): MH 252.1609

Example 22

3-O-methoxymethyldeacetylanisomycin (R=H, X=CH$_2$OCH$_3$)

$^1$H NMR (CDCl$_3$): δ=2.50–2.78 (3H, m), 2.84 (1H, dd, J=13.5, 6.3 Hz), 3.37 (3H, s), 3.32–3.50 (1H, m), 3.68 (1H, m), 3.76 (3H, s), 4.21 (1H, m), 4.59 (1H, d, J=6.9 Hz), 4.72 (1H, d, J=6.9 Hz), 6.81 (2H, d, J=8.4 Hz), 7.12 (2H, d, J=8.4 Hz) MS(FAB): m/z 268 (MH$^+$) High resolution mass spectrum(FAB): Measured: m/z 268.1549; Calculated (C$_{14}$H$_{22}$NO$_4$): MH 268.1561

Example 23

3-O-(2-methoxyethoxy)methyldeacetylanisomycin
(R=H, X=CH$_2$OCH$_2$CH$_2$OCH$_3$)

$^1$H NMR (CDCl$_3$): δ=2.69 (1H, d, J=11.3, 5.8 Hz), 2.71 (1H, dd, J=12.7, 7.1 Hz), 2.84 (1H, dd, J=13.9, 6.0 Hz), 3.40 (3H, s), 3.41–3.62 (4H, m), 3.72–3.82 (2H, m), 3.81 (3H, s), 3.86–4.05 (1H, m), 4.28 (1H, ddd, J=8.5, 6.0, 2.5 Hz), 4.61 (1H, d, J=6.9 Hz), 4.81 (1H, d, J=6.9 Hz), 6.83 (2H, d, J=8.7 Hz), 7.14 (2H, d, J=8.7 Hz) MS(FAB): m/z 312 (MH$^+$) High resolution mass spectrum(FAB): Measured: m/z 312.1811; Calculated (C$_{16}$H$_{26}$NO$_5$): MH 312.1813

Experiment 1: Measurement of stability of anisomycin derivatives in rat plasma

To investigate the stability of the present compounds in rat plasma, the half-life thereof was measured. For the measurement, an approximately 0.25 mg portion of each test compound was dissolved in 150 µl of rat plasma, and the solution was incubated at 37° C. Aliquots were taken over specific periods of time, and the amount of residual anisomycin derivative was measured by HPLC to determine the half-life thereof.

TABLE 1

| Test Compound | Half-life |
| --- | --- |
| Compound of Example 1 | No decomposition |
| Compound of Example 2 | No decomposition |
| Compound of Example 5 | No decomposition |
| Compound of Example 11 | No decomposition |
| Compound of Example 15 | 400 minutes |
| Compound of Example 22 | No decomposition |
| Anisomycin | 3 minutes |

Experiment 2: Measurement of inhibitory activity of anisomycin derivatives on proliferation of FM3A culture The proliferation-inhibiting activity of the present compounds against a culture of FM3A cells derived from mouse mammary tumor was investigated. Into each well of a 96-well microplate was added 50 μl of $10^5$ cells/ml of FM3A cells, which had been suspended in a Dulbecco-modified Eagle culture medium containing 10% fetal calf serum. The $IC_{50}$ (50% proliferation inhibition concentration) was calculated based on the number of surviving cells for a prescribed concentration of the test compounds. The results are shown in Table 2.

TABLE 2

| Test Compound | $IC_{50}$ (ng/ml) |
| --- | --- |
| Compound of Example 1 | 60 |
| Compound of Example 15 | 39 |
| Compound of Example 16 | 39 |
| Compound of Example 17 | 30 |
| Compound of Example 18 | <20 |
| Compound of Example 22 | 62 |
| Anisomycin | 20 |

Experiment 3: Measurement of antifungal activity of anisomycin derivatives

The growth-inhibiting activity of the present compounds against various fungi was investigated. Into each well of a 6-well microplate, 0.3 ml of a solution of each test compound and 2.7 ml of a sterile solution of potato dextrose agar culture medium (kept at a temperature of about 50° C.) were added. After solidification, 5 μl from each suspension of test cells (yeast: approx. $10^3$ cells/ml; mold: approx. $10^4$ spores/ml) was inoculated onto the above-mentioned agar medium, and the cultures were maintained at 25° C. for 7 days. The growth of the test cells was observed, and the minimum concentration (MIC value) was determined at which complete inhibition of growth occurred. The test compounds were used after adjustment to 1 mg/ml with dimethylsulfoxide and dilution with distilled water. The results are shown in Table 3.

TABLE 3

| Fungus | Compound of Example 18 | Anisomycin |
| --- | --- | --- |
| *Candida albicans* | 50 μg/ml | 100 μg/ml |
| *Saccharomyces cereviceae* | 25 | 12.5 |
| *Cryptococcus neoformans* | 3.1 | 25 |
| *Aspergillus fumigatus* | 50 | >100 |
| *Mucor rouxii* | 50 | >100 |

Experiment 4: Antitumor effect of anisomycin derivatives in vivo

Into one group of 5 CDF1 mice, $1 \times 10^6$ P388 leukemia tumor cells were intraperitoneally transplanted. Beginning the next day, a 10 mg/kg portion of the test compound dissolved in 0.2 ml of a solution containing an equal volume of dimethylsulfoxide and saline was administered to the mice intraperitoneally once a day for 10 days. The increase in the life span of the mice in days (ILS) was determined according to the following equation:

$$ILS(\%) = \frac{T - C}{C} \times 100$$

TABLE 4

| Test compound | ILS (%) |
| --- | --- |
| Compound of Example 18 | 44 |
| Anisomycin | 0 |

EFFECT OF THE INVENTION

The present compounds are less decomposable in plasma in comparison with anisomycin, and possess high stability in vivo. Also, their cytotoxicity against tumor cells is at least as strong as that of anisomycin. The present compounds also exhibit antifungal activity, and are very useful as anticancer, antifungal and antiprotozoan agents.

What is claimed as new and desired to be secured by letters Patent of the United States is:

1. An anisomycin compound of the following formula or a pharmaceutically acceptable salt thereof:

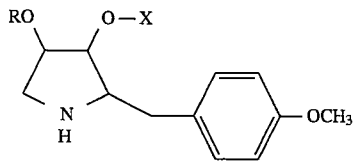

wherein R is a hydrogen atom or a saturated or unsaturated alkylcarbonyl group having 1 to 18 carbon atoms; and X is either a carbamoyl group of the formula —$CONR^1R^2$ or an alkyl group of the formula —$CH_2R^3$, wherein each of $R^1$ and $R^2$ is independently a hydrogen atom, a linear or cyclic alkyl group having 1 to 6 carbon atoms which may be substituted, or a phenyl group which may be substituted, and $R^3$ is a hydrogen atom, an alkyl group having 1 to 6 carbon atoms, or an alkoxy group having 1 to 6 carbon atoms, which may be substituted; with the proviso that (a) when $R^1$ or $R^2$ is a substituted linear or cyclic alkyl group having 1 to 6 carbon atoms, the group is substituted with one or more substituents selected from the group consisting of halogen atoms, hydroxy groups, carboxy groups, alkoxy groups of 1 to 4 carbon atoms and cyano groups, (b) when $R^1$ or $R^2$ is a substituted phenyl group, the phenyl group is substituted with one or more substituents selected from the group consisting of halogen atoms, hydroxy groups, carboxy groups, alkoxy groups of 1 to 4 carbon atoms, cyano groups, alkyl groups of 1 to 6 carbon atoms, alkenyl groups of 1 to 6 carbon atoms, alkynyl groups of 1 to 6 carbon atoms, halogenated alkyl groups of 1 to 6 carbon atoms, halogenated alkenyl groups of 1 to 6 carbon atoms, and halogenated alkynyl groups of 1 to 6 carbon atoms, and (c) when $R^3$ is a substituted alkoxy group having 1 to 6 carbon atoms, said group is substituted with a substituent selected from the group consisting of, one or more halogen atoms, hydroxy groups, carboxy groups, alkoxy groups of 1 to 4 carbon atoms, cyano groups, alkyl groups of 1 to 6 carbon atoms, alkenyl groups of 1 to 6 carbon atoms, alkynyl groups of 1 to 6 carbon atoms, halogenated alkyl groups of 1 to 6 carbon atoms, halogenated alkenyl groups of 1 to 6 carbon atoms, or halogenated alkynyl groups of 1 to 6 carbon atoms.

2. The anisomycin derivative of claim 1, wherein R is a hydrogen atom and X is —$CONR^1R^2$.

3. The anisomycin derivative of claim 1, wherein R is a hydrogen atom and X is —$CH_2R^3$.

4. The anisomycin derivative of claim 1, wherein R iS an acyl group having 1 to 18 carbon atoms and X is a carbamoyl group which may be substituted with an alkyl group having 1 to 6 carbon atoms.

5. A method of treating or preventing a fungal infection, comprising administering an effective amount of the anisomycin of claim 1 to a patient in need thereof.

6. A method of treating or preventing a protozoa infection, comprising administering an effective amount of the anisomycin of claim 1 to a patient in need thereof.

7. A pharmaceutical composition comprising an anisomycin compound as set forth in claim 1 in a pharmaceutically acceptable carrier.

8. The method of treating leukemia comprising administering to a patient in need thereof, an effective amount of an anisomycin compound as set forth in claim 1.

9. The compound 4-O-dodecanoyl-3-O-carbamoyldeacetylanisomycin.

10. The compound 3-O-methylcarbamoyl-deacetylanisomycin.

11. The compound 4-O-acetyl-3-O-carbamoyldeacetylanisomycin.

12. The compound 4-O-hexanoyl-3-O-carbamoyldeacetylanisomycin.

13. The compound 4-O-heptanoyl-3-O-carbamoyldeacetylanisomycin.

14. The compound 3-O-methoxymethyldeacetylanisomycin.

15. The compound 3-O-carbamoyldeacytylanisomycin.

* * * * *